United States Patent [19]

Hall

[11] Patent Number: 5,006,716
[45] Date of Patent: Apr. 9, 1991

[54] METHOD AND SYSTEM FOR DIRECTIONAL, ENHANCED FLUORESCENCE FROM MOLECULAR LAYERS

[75] Inventor: Dennis G. Hall, Pittsford, N.Y.

[73] Assignee: Research Corporation Technologies, Inc., Tucson, Ariz.

[21] Appl. No.: 313,763

[22] Filed: Feb. 22, 1989

[51] Int. Cl.$^5$ .................... G01N 21/62; G01N 21/64
[52] U.S. Cl. .................... 250/458.1; 250/368; 250/459.1; 250/461.1; 250/483.1; 250/487.1; 436/171; 436/172
[58] Field of Search .......... 250/458.1, 459.1, 484.1 R, 250/483.1, 487.1, 368, 461.1, 461.2; 436/171, 172

[56] References Cited

U.S. PATENT DOCUMENTS

| | | | |
|---|---|---|---|
| 4,649,280 | 3/1987 | Holland et al. | 250/459.1 |
| 4,804,850 | 2/1989 | Norrish et al. | 250/459.1 |
| 4,882,288 | 11/1989 | North et al. | 436/525 |

OTHER PUBLICATIONS

"Waveguide mode enhancement of molecular fluorescence"-W. R. Holland and D. G. Hall, 1985, *Optics Letters*, vol. 10, pp. 414 to 416.
"Light emission from surface-plasmon and waveguide modes excited by N atoms near a silver grating"-Adams et al., *Physical Review B, Condensed Matter*, Third Series, vol. 25, No. 6, pp. 3457 to 3461.
"Thin grating couplers for integrated optics: an experimental and theoretical study"-Dalgoutte et al., Dec., 1975, vol. 14, No. 12, Applied Optics, pp. 2983 to 2998.
"Elastic scattering, absorption, and surface-enhanced Raman scattering by concentric spheres comprised of a metallic and a dielectric region"-Kerker et al., *Physical Review B*, vol. 26, No. 8, pp. 4052 to 4063, Oct. 15, 1982.

*Primary Examiner*—Constantine Hannaher
*Assistant Examiner*—Edward J. Glick
*Attorney, Agent, or Firm*—Scully, Scott, Murphy & Presser

[57] ABSTRACT

Propagation modes within a corrugated optical waveguide are used to excite fluorescence from a layer of material which defines a wall of the waveguide. The fluorescence is emitted at discrete angles, which are a function of the wavelength and polarization of the emitted fluorescence. The intensity of fluorescence detected at the discrete angles of detection can approach 2000 times the intensity detected from the same fluorescence material coated on a glass slide. These features enable a number of tests to be performed simultaneously on an unknown sample, as well as providing a finer and more accurate determination of concentration of a substance over prior art systems.

42 Claims, 5 Drawing Sheets

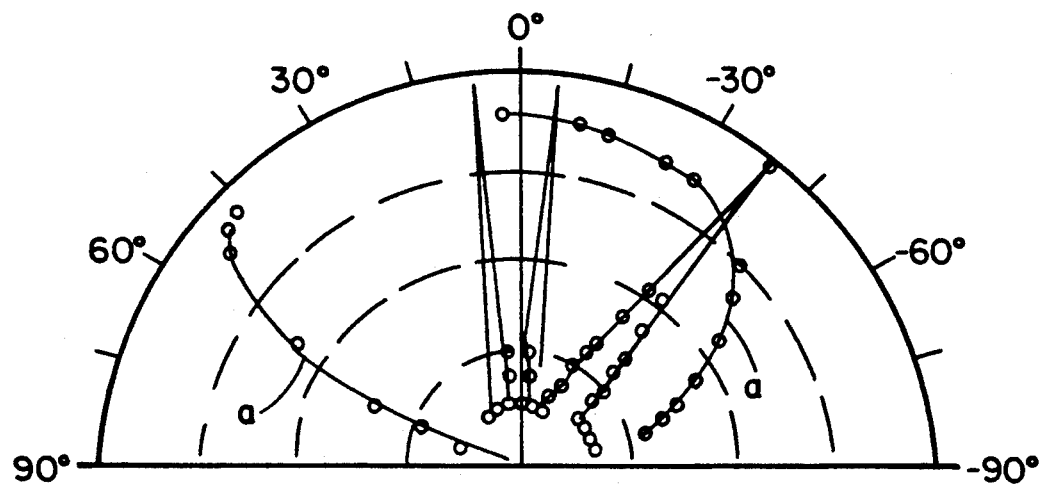
FIG. 3 ANGULAR DISTRIBUTION OF THE ENHANCED TM-POLARIZED FLUORESCENCE AT THE WAVELENGTH 585 nm FROM A <u>CORRUGATED</u> STRUCTURE, AS IN FIGURE 1. 0° MARKS THE NORMAL TO THE SAMPLE SURFACE.

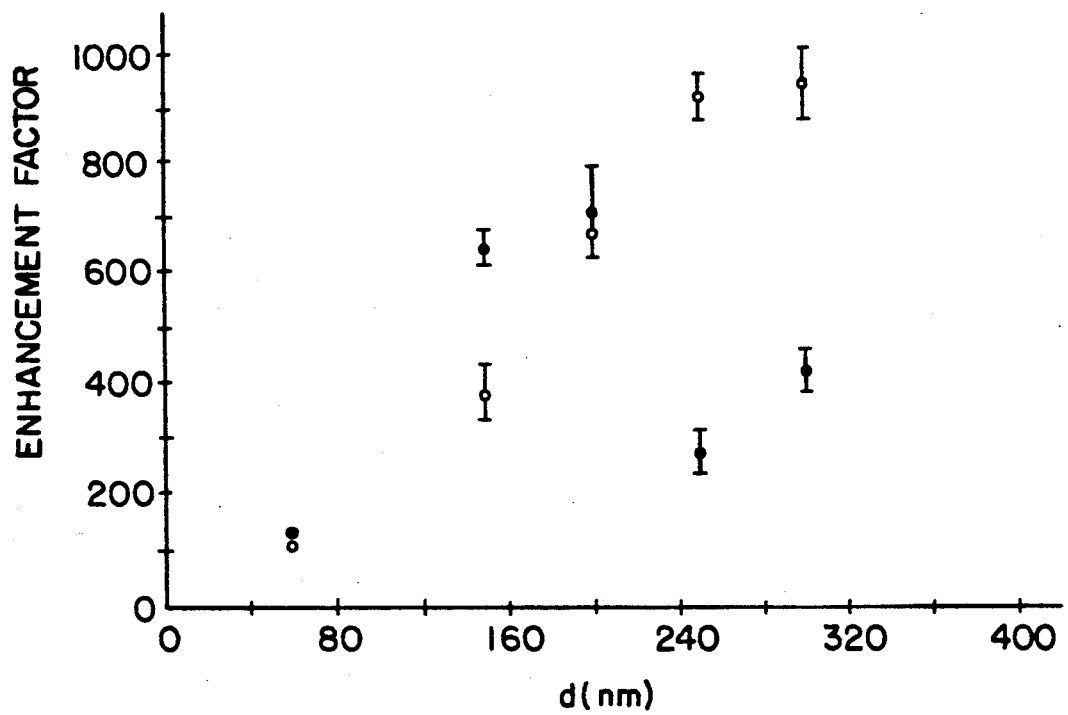
FIG. 4 ENHANCEMENT FACTORS VS. WAVEGUIDE THICKNESS d OF THE TM-POLARIZED RESONANT FLUORESCENT SIGNAL EMITTED BY THE SURFACE PLASMON MODE. THE SOLID DOTS DENOTE THE ENHANCEMENT FACTORS FOR TM-POLARIZED EXCITING LIGHT, THE CIRCLES DENOTE THE ENHANCEMENT FACTORS FOR TE-POLARIZED EXCITING LIGHT.

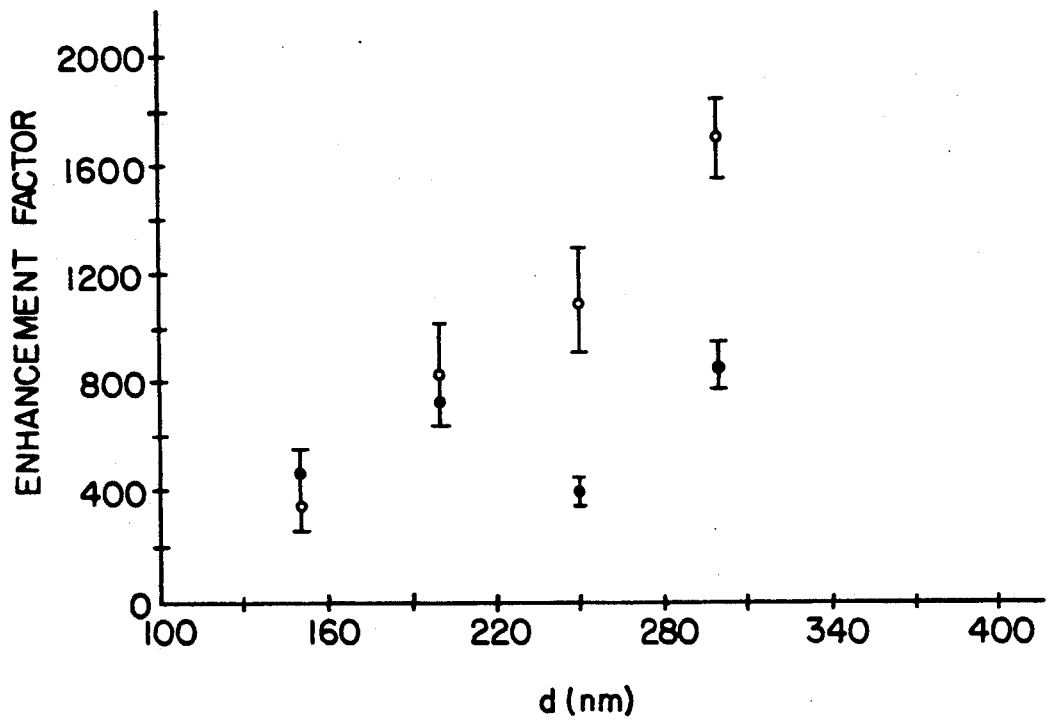
FIG. 5 ENHANCEMENT FACTORS VS. WAVEGUIDE THICKNESS d OF THE TE-POLARIZED RESONANT FLUORESCENT SIGNAL EMITTED BY THE $TE_0$-MODE. THE SOLID DOTS DENOTE THE ENHANCEMENT FACTORS FOR TM-POLARIZED EXCITING LIGHT, AND THE CIRCLES DENOTE THE ENHANCEMENT FACTORS FOR TE-POLARIZED EXCITING LIGHT.

METHOD AND SYSTEM FOR DIRECTIONAL, ENHANCED FLUORESCENCE FROM MOLECULAR LAYERS

BACKGROUND OF THE INVENTION

The present invention relates to methods and systems for directional, enhanced fluorescence from molecular layers, including its use in determining the presence or absence of a substance with a fluorescent component.

The invention is an improvement on the fluorescent assay method and apparatus described in U.S. Pat. No. 4,649,280, which issued Mar. 10, 1987 to Holland and Hall. Fluorescent assay systems typically employ optical detectors to detect the light emitted from a fluorescing substance. When light of a wavelength known to excite the fluorescent component of a particular substance is incident on an unknown sample, the presence (or absence) of the substance in the sample may be indicated by detecting the presence (or absence) of a fluorescent emission. Well known to the art is that the excitation and emission wavelengths of a fluorescent material are different.

Any methods of chemical analysis, including fluorescent assay systems, are improved by increasing the reliability of their results. U.S. Pat. No. 4,649,280 describes a method which increases the intensity of the fluorescent light emitted from the sample. This increase decreases the sensitivity required in the optical detector to determine the presence of a substance, which allows the detection of smaller quantity of a substance in a sample.

The method and apparatus described in the patent increased the light intensity of a fluorescing substance by employing an optical waveguide to generate a strong electromagnetic field in the vicinity of a film of fluorescent material, and particularly from the layers of molecules of the material attached to a wall of the optical waveguide. The excitation radiation which was incident on the fluorescent material was self-coupled to the waveguide to support the propagation of the modes which generated the strong field. This combination caused more intense fluorescence (i.e., intensity of the fluorescence) relative to that excited by radiation incident on conventional systems (i.e., fluorescent material coated on a glass slide). The strong field generated by the propagating modes was responsible for the increased fluorescence, and the increase was a function of the dimensions of the waveguide which supported the waveguide modes. The intensity of the fluorescence could be increased nearly 200 times that of conventional systems.

A number of problems were presented with the prior art systems.

The first problem was that the fluorescence emitted at a given wavelength from conventional systems and the system described in U.S. Pat. No. 4,649,280 was diffusely distributed about a normal to the flat surface of the fluorescent material. The result of this diffuse distribution was that most of the fluorescence emitted by the sample was not collected by the photodetectors. This diffuse distribution was compensated to some extent by the increased enhancement from the system described in U.S. Pat. No. 4,649,280; however the basic inefficient distribution for detection purposes remained. Since only a fraction of the fluorescence was detected, the prior art measurement techniques and systems were inherently less efficient than one that can make use of most or all of the fluorescence at a given wavelength, as provided by the present invention.

Another problem with conventional systems and the improved system of U.S. Pat. No. 4,649,280 was that they only determined the presence, absence and, to a limited degree, the concentration of a material in a sample. Also absent from these systems were other tests which would further indicate the presence or absence of a fluorescent material in a sample. Finally, if the fluorescent test was inconclusive, or if a check of the results was desired to increase the conclusiveness of the analysis, a completely separate method of analysis had to be used. This added expense to the analysis and was time consuming.

W. R. Holland et al., *Optics Letters*, Vol. 10, No. 8, pp. 414-416 (August 1985) also describes waveguide mode enhancement of molecular fluorescence, as described in the aforementioned patent, and ascribes the enhancement to near field interaction between the fluorescent molecules and the waveguide modal fields. A. M. Glass et al., *Optics Letters*, Vol. 5, No. 9, pp. 368-370 (September 1980), also reports the enhancement of fluorescent material deposited on a silver film.

SUMMARY OF THE INVENTION

The present invention provides a method and system for directional, enhanced fluorescence from molecular layers which simultaneously or consecutively enables a multiplicity of tests to be performed to determine the presence, absence or concentration of a material in a sample.

Another objective of the present invention is to provide a method and system for directional, enhanced fluorescence from molecular layers which detects substantially all the fluorescent radiation at a given wavelength.

Another objective of the present invention is to accomplish the aforementioned objectives in a relatively simple and inexpensive manner.

Utilizing the method and system of the present invention, the fluorescent light emitted at a given wavelength is radiated at discrete angles with respect to the normal to the surface of the material. These discrete angles of emission enable photodetectors to be arranged to detect most of the fluorescent emission. The emission angles are a function of the wavelengths of the emitted light as well as the state of polarization of the emitted light and the waveguide thickness. The signal detected by the present invention can have an enhancement factor close to 2000. The "enhancement factor" is defined as the fluorescent intensity collected from the examined system divided by the fluorescent signal collected from a conventional system. The combination of directional emission, such distinct angles having a functional relationship to wavelength, polarization and thickness, as well as increased enhancement, allows a number of features of a fluorescent emission to be analyzed simultaneously and with a minimum of hardware, leading to more accurate results in a simpler and less time consuming manner.

In general, the present invention relates to the method of improving the detection, identification, and enhancement of fluorescence of a material comprising the steps of:

(a) depositing a layer of the material on a waveguide with corrugated surface(s) which supports propagation modes for optical radiation at the wavelengths of absorption by and fluorescence from the material, (b) exciting the fluorescence of the material through the waveguide propagation modes at the wavelength of absorption by said material and at discrete angles of emission to the normal to its surface, and (c) detecting the fluorescence at said discrete angles from the film's normal.

In accordance with the present invention, the basic structure of the waveguide mode enhancement of molecular fluorescence system is modified by adding corrugations to the waveguide structure. In existing waveguide mode enhancement systems the modes of an optical waveguide are used to generate a strong electromagnetic field in the vicinity of a film of fluorescent material, and particularly from the layer of molecules of the material attached to a wall of the optical waveguide. The propagation region of the waveguide is defined by a layer of dielectric material. Another wall of the waveguide is a film of conductive, reflective material on the surface of the dielectric layer opposite that on which the layer of fluorescent molecules is deposited. The excitation radiation which is incident on the fluorescent material is self-coupled to the waveguide to support the propagation of the modes which generate the strong field. The enhancement factor of this basic waveguide mode enhancement system can be up to 200.

The addition of corrugations to the basic waveguide enhancement system provides the directionality, polarization discrimination, increased enhancement, and emission wavelength selectivity to the emitted fluorescent light described above.

The directionality of the fluorescence emitted at a given wavelength is believed to be attributable to the grating induced emission from optical waveguide modes supported by the structure. The operation of the resulting directionality may be appreciated by considering an optical waveguide with a perfectly smooth surface and light of a supported mode propagating within it. Such light incident on the interior waveguide boundary evidences total internal reflection and is never detected at points outside the waveguide. A corrugation pattern imposed on the waveguide boundary creates a deficiency in the smoothness, allowing the light incident on the waveguide boundary to be diffracted out of the waveguide. Thus, the corrugations act in the first order as a diffraction grating on the incident light. It is well known in the art that light incident on a diffraction grating demonstrates an intensity distribution with maxima of intensity at discrete angles with respect to a normal to the mean grating surface. The discrete angles are a function of the grating dimensions and the wavelength of the incident light. With a fluorescent sample overlaying the waveguide boundary, the fluorescence induced is also emitted directionally. Therefore, for each emitted wavelength there may be a multiplicity of discrete angular emissions corresponding to the orders of diffraction.

The polarization discrimination is believed due to the emissions excited by the various TM and TE modes supported by the waveguide. It is a well known property of all waveguides that, because of the energy distributions in each particular mode, each mode of the same wavelength has a different effective index of refraction in the waveguide medium. Therefore, two modes of an equivalent wavelength propagating in the waveguide have different ray-paths or, equivalently, have different incident angles at the waveguide boundaries. The corrugated waveguide boundary with the fluorescent layer was analogized to a diffraction grating above. It is well known that light rays of the same wavelength incident on a diffraction grating at different angles will have different angles of diffraction. Since the different TM and TE modes of the same wavelength have different incident angles on the corrugated surface, they have different angles of diffraction. With a fluorescent sample over laying the waveguide boundary, the fluorescent induced is also emitted directionally as a function of propagation mode.

Additionally, the effective indices of refraction are sensitive to almost all features of the waveguide, including waveguide thickness, dielectric layer, 16, dielectric material, conductive layer, 14, conductive material, etc. Therefore the discrete angles of emission corresponding to each waveguide propagation mode will shift with changes in these properties.

The increased enhancement of the emitted light is believed due to the concentration of the emitted light at angles to the normal which are discrete rather than a diffuse fluorescent emission. The enhancement from this mechanism acts in conjunction with the enhancement due to the basic waveguide system discussed above and in U.S. Pat. No. 4,649,280.

It should be noted that the foregoing theoretical discussion is intended to provide the inventor's present understanding of the phenomena observed in the invention, and is not to be regarded as a definitive statement on how the invention functions or to limit the invention in any way.

BRIEF DESCRIPTION OF THE DRAWINGS

FIG. 3 is a plot illustrating the fluorescence as a function of angle detected, $\phi_d$, from the normal to a particular embodiment of the structure illustrated in FIGS. 1 and 2.

FIG. 4 is a plot showing the enhancement factor as a function of the thickness of the layer d for particular embodiments of the structures shown in FIGS. 1 and 2 for a particular wavelength emitted attributed to the $TM_o$ waveguide mode, where the incident light is TM and TE polarized.

FIG. 5 is a plot showing the enhancement factor as a function of the thickness of the layer d for a particular embodiment of the structures shown in FIGS. 1 and 2 for a particular wavelength emitted attributed to the $TE_o$ waveguide mode, where the incident light is TM and TE polarized.

DETAILED DESCRIPTION

Figure 1:
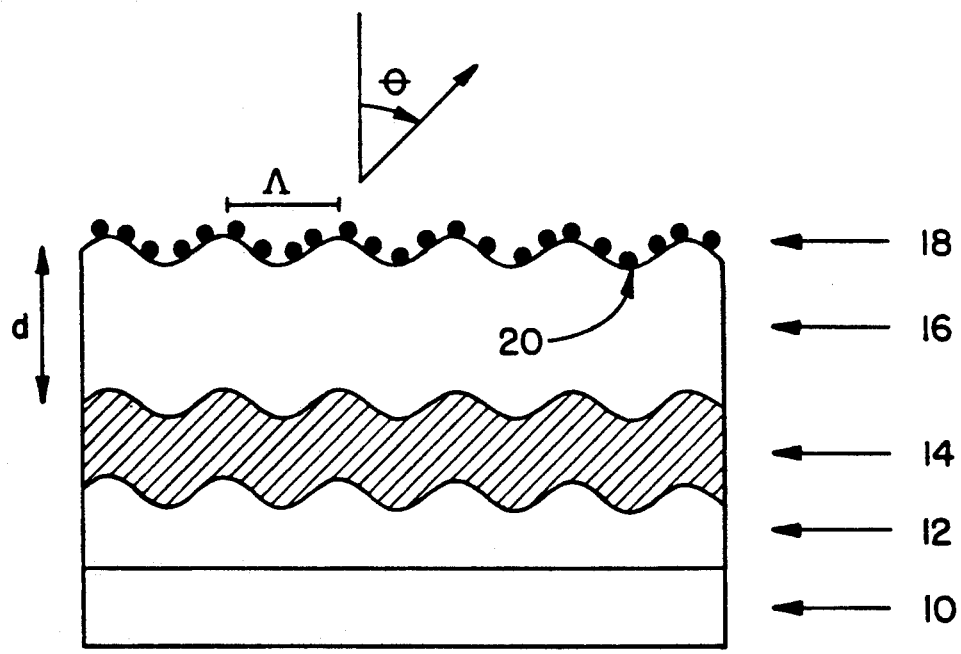
FIG. 1 is a schematic diagram of a cross section of a structure which emits directional, enhanced fluorescence from molecular layers.

Referring to FIG. 1, a substrate, 10, which may be a rectangular glass slide is coated with a grated layer, 12. The grated layer, 12, in one configuration, is created by depositing a layer of photoresist on the glass substrate, imposing an interference pattern on the photoresist, and then developing the photoresist. Spinning methods commonly employed in research laboratories and in the semiconductor industry can be used to achieve a sufficiently uniform thickness of the photoresist on the slide. In one embodiment the entire slide was coated with a photoresist with a thickness of approximately 300 nm. The particular thickness is unimportant, as long as it can support the minimum to maximum requirements of the corrugation structure, approximately 50 nm peak to valley in one particular corrugated structure, 12. The area of the interference pattern and the resulting corrugation pattern does not have to cover the whole slide. An area of 1 cm$^2$ was found to be adequate. The photoresist pattern may be recorded by illuminating the photoresist with the two recombined beams split off a common laser source. In a particular embodiment the periodicity of the corrugation, $\Lambda$ in FIG. 1, was 0.636 $\mu$m. The developed photoresist produces a shallow corrugated grating structure, 12. This produces a shallow, corrugated photoresist underlayer which corrugation appears on later layers impressed upon the developed photoresist. Other methods of creating shallow gratings, such as embossing, may be used depending on the particular manufacturing environment. In a commercial setting relating to medical diagnostics, it is contemplated manufacturers would use stamped plastic gratings of predetermined dimensions selected according to the test to be applied to an unknown sample. Such grating manufacturing technology currently exists.

Periods of corrugation in the range 0.1–1.0 $\mu$m are contemplated for these gratings.

The remainder of the structure which provides the system for directional, enhanced fluorescence from molecular layers shown in FIG. 1 is created in a manner analogous to that described in U.S. Pat. No. 4,649,280, the disclosure of which is incorporated herein by reference thereto. Grating, 12, is coated with conductive layer, 14, of conductive, reflective material. Vacuum deposition techniques may be used. The thickness of conductive layer, 14, is on the order of 50 nm, depending on the metal used. A dielectric layer, 16, of thickness d of a dielectric material is deposited upon conductive layer, 14. Lithium Fluoride (LiF) among other dielectric materials may be used. The thickness, d, of dielectric layer, 16, is critical in its relation to the wavelength(s) of the exciting, incident radiation and the emitted wavelength, as will be apparent from FIGS. 4 and 5, but is nominally on the order of 20–500 nm. Conductive layer, 14, and dielectric layer, 16 may be made using high vacuum thermoevaporation techniques.

Fluorescent material layer, 18, is deposited over dielectric layer, 16. It is illustrated as the row of spheres to schematically show the molecular layer at interface, 20, between fluorescent material layer, 18, and dielectric layer, 16. The fluorescent component in the fluorescent material layer may be bound to the molecule of interest in accordance with techniques used in fluorescent assays. The thickness of fluorescent material layer, 18, is desirably on the order of single molecules in thickness. This is not an absolute requirement and thickness up to an optical wavelength, i.e., between 1 and 10 $\mu$m, is adequate. It must be thin enough to allow exciting light to reach molecules near interface 20, so that waveguide propagation modes are excited through coupling with the fluorescent molecules absorbing the incident light.

By way of example, fluorescent material layer, 18, may be applied to the system once conductive layer, 14, and dielectric layer, 16, are applied. Fluorescent material layer, 18, may be applied using slow heating evaporation of a fluorescent dye at very low pressure. Alternative methods are well known in the art and include spin coating and dipping.

Fluorescent material layer, 18, dielectric layer 16, and layer of reflective conductive material 14 define an optical waveguide which supports a plurality of propagation modes. Conductive layer, 14, has corrugated structure analogous to grating, 12, and follows the contours of grating, 12. Dielectric layer, 16, has corrugated structure analogous to conductive layer, 14, and follows the contours of conductive layer, 14. Fluorescent material layer, 18, has corrugated structure analogous to dielectric layer, 16 it having been deposited on dielectric layer, 16.

It is apparent that the corrugated structure in the film is not limited to a corrugation pattern in two dimensions as shown in FIG. 1. Grated layer, 12, may have superimposed gratings oriented in a number of directions with respect to the grating normal, the normal to such corrugated structures in general defined as the normal to the plane seen from a point an infinite distance above the corrugated surface. One method of achieving such overlapping corrugated structure is to deposit a layer of photoresist on a glass substrate and illuminate the photoresist with two or more interference patterns oriented at different directions with respect to the photoresist surface normal prior to developing the photoresist. The disoriented interference patterns may be achieved using two or more recombined beams split off two or more common laser sources, each pair of split beams recombined at the same point on the layer of photoresist, but the plane defined by each pair of beams distinctly oriented with respect to the surface normal at the common point of incidence. Similarly, a plastic grating commercially manufactured could be made with superimposed non-parallel gratings.

The corrugated surface comprised of a number of such superimposed gratings has a number of non-parallel "surface profiles", a "surface profile" defined as the cross-section of the surface on a plane normal to the corrugated surface oriented so that one of the regular corrugation patterns is displayed.

Figure 2:
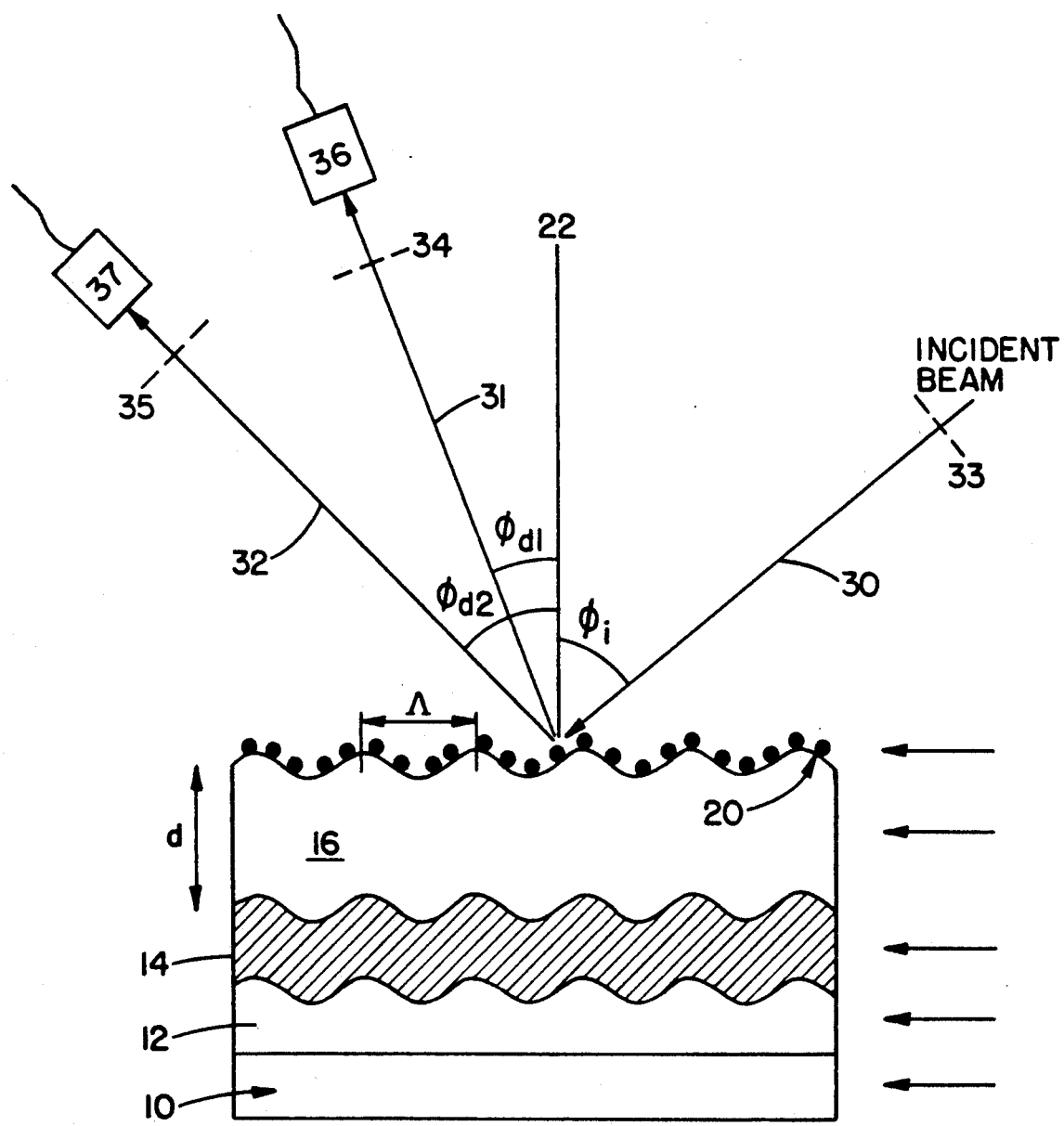
FIG. 2 is a schematic diagram illustrating the operation of the invention and the improved method for stimulating directional, enhanced fluorescence from molecular layers.

Referring to FIG. 2, incident beam, 30, of wavelength $\lambda_i$ passes through polarizer, 33 and is incident at angle $\phi_i$ with respect to normal, 22. Both the polarizer 33 and a specific angle of incidence $\phi_i$ are optional, and serve to enhance the properties of the present invention, as described below. Due to the interaction of incident beam, 30, with fluorescent layer 18, one or more fluorescent beams of wavelength $\lambda_f$ appear, shown in FIG. 2 as fluorescent beam 31, and fluorescent beam 32. Fluorescent beam 31, is emitted at angle $\phi_{d1}$, with respect to normal, 22, passes through polarizer 34, and is detected by optical detector, 36. Likewise, fluorescent beam, 32, also of wavelength $\lambda_f$, is emitted at angle $\phi_{d2}$, with respect to normal, 22, passes through polarizer 35, and is detected by optical detector, 37. Each discretely emitted fluorescent beam is either TM or TE polarized, and the polarizers, 34, 35, prior to detection can be rotated to verify this. It is seen that polarizers 34, 35 are also optional to the present invention, and serve to only verify the polarization of the emitted wave. The intensity of the fluorescent beam is a function of the polarization of the incident beam, 30. Therefore, the intensity detected at the optical detectors, 36, 37, varies as polarizer, 33, is rotated. Each fluorescent beam is attributed to a particular propagation mode in the waveguide, and the directionality is attributed to the corrugation structure. As the waveguide thickness, d, increases, more modes appear, and therefore more discrete fluorescent beams appear. Furthermore, each mode may interact with more than one order of the surface corrugation, thereby having more than one discrete emission angle attributable to one waveguide mode.

In one particular configuration of FIG. 2, the fluorescent material, 18, is Rhodamine B and the dielectric layer, 16 is LiF. The thickness of the dielectric layer, d=150 nm and the period of the surface profile, $\Lambda=0.636$ micrometer. Incident beam, 30, originates from an Argon ion laser with wavelength $\lambda_i=514.5$ nm and power attenuated to 0.1 milliwatt. The angle of incidence $\phi_i$ is adjusted to approximately 15° to maximize the fluorescent output. Optical detectors, 36, 37, may be used with a monochrometer or other filter to select $\lambda_f=585$ nm, and polarizers, 34 or 35, are moved through the angles of detection with respect to the normal.

Referring to FIG. 3, the sharp peak at approximately −38° shows that a TM polarized beam of wavelength 585 nm is present at −38°. A similar peak is also expected at +38°, but its actual detection was prevented due to the experimental apparatus. With the polarizer oriented in a TE direction, the sharp peak at ±5° of wavelength 585 nm demonstrates a TE polarized beam discretely emitted at that angle. The fluorescent beam at −38° is attributed to the $TM_o$ waveguide mode interacting with the 1st order of the grating. The fluorescent beam at ±5° is attributed to the $TE_o$ mode of the waveguide interacting with the 1st order of the grating.

The diffuse pattern, a, in FIG. 3 is the fluorescent emission as a function of the detection angle for an uncorrugated waveguide. The wavelength of the detected light is 585 nm and the diffuse distribution is attributed to diffuse emission from each waveguide mode. Therefore, unpolarized light is detected at each point of detection. The radial scale is normalized separately for the peaked and the diffuse patterns. The diffuse pattern is for $\Lambda \rightarrow \infty$ in FIG. 1, i.e., a flat surface. The peaks have an enhancement factor of 200 to 2000 while the enhancement factor of the diffuse emission does not exceed 200.

FIG. 3 demonstrates that if a known material labeled with a fluorescent component fluoresces at 585 nm, its use in a system as shown in FIG. 2 will result in strong peaks detected at ±5° and ±38°. Since the angle of emission is dependent on the interaction of the particular wavelength with the corrugated structure, the presence of the material in an unknown sample labeled with a fluorescence is indicated by fluorescent emission at angles characteristic of the material.

It is further noted that the corrugated waveguide could be manufactured as described above using an aperiodic grating, resulting in an aperiodic waveguide surface.

Referring to FIGS. 4 and 5, the enhancement of the excited fluorescence is shown for a system of the type described in FIG. 2. FIGS. 4 and 5 are another exemplary case where the angle of incidence of the 514.5 nm excitation beam is approximately 15°; the fluorescent material is Rhodamine B; the dielectric layer is LiF; the detector is placed at the peak detection angle for the particular wavelength detected (585 nm) and the type of polarization. The intensity detected is then compared with the fluorescent intensity detected at that angle from the same quantity of molecules deposited on a glass substrate and similarly excited. The ratio of the former signal to the latter is the enhancement factor defined above In FIG. 4, the enhancement factor is plotted as a function of d in FIGS. 1 and 2 for the 585 nm TE wave excited by the $TE_o$ mode for incident wave TM or TE polarized. In FIG. 5, the enhancement factor is plotted as a function of d In FIGS. 1 and 2 for the 585 nm TM wave excited by the $TM_o$ mode for an incident wave TM or TE polarized. From FIG. 4 it is seen that the enhancement factor for TE-polarized emission can be as high as 1000 while FIG. 5 shows that the enhancement factor for TM-polarized emission can be close to 2000.

FIGS. 4 and 5 demonstrate that the dielectric layer thickness ("d" in FIGS. 1 and 2) can be set to maximize the enhancement at a particular angle of detection (equivalently, from one of the particular waveguide modes). Alternatively, d may be set to give roughly equal and substantially increased enhancement at two or more angles of detection (equivalently, from two or more particular waveguide modes). These figures demonstrate that when testing an unknown sample for the presence or concentration of a particular material, the selection of d will substantially improve the ability to detect the presence or concentration of the material.

The increased detection ability and the unique angular and polarization features corresponding to a particular wavelength can be combined in a commercial embodiment which simultaneously performs different analyses on an unknown sample, leading to more accurate results in less time, with a minimum of hardware. A configuration like that of FIG. 2 could have one or more optical detectors fixed at those angles corresponding to the discrete angular emissions of a particular wavelength excited by propagation modes of a waveguide of set dimensions and materials. The detection of emission from an unknown fluorescent material layered on the waveguide at the various detectors would show the material fluoresced at the known wavelength. As emission at that wavelength would correspond to a known material. The system eliminates the need of a monochrometer to test for the material by determining the wavelength. A polarizer before detection would further confirm the presence of the particular wavelength corresponding to the material. Finally, the increased enhancement would provide the ability to determine concentration of the material, once reference concentrations and peak limits are determined.

We claim:

1. A method of enhancing and improving the detection of a fluorescent emitting material comprising the steps of:

(a) depositing a film of a fluorescent emitting material on a waveguide with a corrugated surface which supports propagation modes for optical radiation at the wavelength of absorption by and fluorescence from said fluorescent emitting material, wherein the waveguide comprises a plurality of layers deposited on a grating, said plurality of layers including a layer of an electrically conductive, light reflective material forming said corrugated surface, a layer of a dielectric material disposed over the conductive, reflective material, and having a thickness between 20 nanometers and 500 nanometers, the depositing step including the step of depositing the fluorescent emitting material on the layer of the dielectric material, wherein the dielectric material maintains the fluorescent emitting material spaced from the conductive, reflective material a distance of between 20 and 500 nanometers, (b) exciting said fluorescence in said film through the waveguide propagation modes at the wavelength of absorption by said fluorescent emitting material and at discrete angles of emission from the film's normal, (c) detecting said fluorescence at discrete angles from the film's normal.

2. The method according to claim 1 wherein waveguide propagation modes at the wavelength of absorption and wavelength of emission of said fluorescent emitting material are excited by light incident on said film opposite said waveguide.

3. The method according to claim 2 wherein said waveguide propagation modes at said wavelength of fluorescence couple with the molecules of said fluorescent emitting material, whereby there is enhanced radiation from said fluorescent surface.

4. The method according to claims 1, 2 or 3 wherein said film is deposited to provide a thin layer of said fluorescent emitting material having a thickness between a diameter of a single molecule of said fluorescent emitting material, and 10 micrometers.

5. The method according to claims 1, 2 or 3 wherein said corrugated surface has uniform periodic structure.

6. The method according to claim 1 wherein said corrugated surface has aperiodic structure.

7. The method according to claims 1, 2 or 3 wherein said corrugated surface has a sinusoidal corrugation profile.

8. The method according to claim 1 wherein said corrugated surface has one or more uniform corrugation profiles in non-parallel planes.

9. The method according to claims 1, 2 or 3 wherein said corrugated surface has at least one uniform corrugation profile in non-parallel planes, said waveguide propagation modes having direction of travel parallel to each non-parallel corrugation profile, and said fluorescence excited by said waveguide propagation modes with different directions of travel lying in different planes with respect to the surface normal.

10. The method according to claim 9 wherein said waveguide propagation modes with different directions of travel are excited by one or more sources of incident light lying in planes with respect to the surface normal which are not co-planar.

11. The method according to claims 1, 2 or 3 wherein said waveguide propagation modes are excited by incident light emitted in single or multiple pulses during the time of detection.

12. The method according to claims 1, 2 or 3 wherein said waveguide propagation modes are excited by incident light emitted in a continuous wave during the time of detection.

13. The method according to claims 1, 2 or 3 wherein said waveguide propagation modes are excited by incident light at angles which maximize the intensity of said waveguide propagation modes.

14. The method according to claim 13 wherein said incident light is from an incoherent source.

15. The method according to claim 13 wherein said incident light is from a laser.

16. The method according to claim 13 wherein the wavelength of said incident light is 515.5 nm and is provided by an Argon ion laser with intensity of about 0.1 milliwatt.

17. The method according to claims 1, 2 or 3 wherein said waveguide propagation modes are excited by incident light of TM or TE polarization.

18. The method according to claims 1, 2 or 3 wherein some or all of said fluorescence at said discrete angles passes through a polarizer before detection.

19. The method according to claims 1, 2 or 3 wherein said fluorescence emitted at discrete angles is detected by optical detectors at fixed angles with respect to the normal to the corrugated surface.

20. The method according to claims 1, 2 or 3 wherein said fluorescence emitted at discrete angles is detected by optical detectors whose angles with respect to the normal to the plane defined by the maxima of the grating may be varied, wherein said discrete angles of emission from the film's normal where said fluorescent emitting material is unknown may be determined by varying the angle of the detectors with respect to the normal.

21. The method according to claim 9 wherein said fluorescence is detected by optical detectors lying in different planes with respect to the surface normal.

22. The method according to claim 21 wherein said fluorescence emitted at discrete angles is detected by optical detectors at fixed angles with respect to the normal to the corrugated surface.

23. The method according to claim 7 wherein said fluorescence emitted at discrete angles is detected by optical detectors whose angles with respect to the normal to the plane defined by the maxima of the grating may be varied, wherein said discrete angles of emission from the film's normal where said fluorescent emitting material is unknown may be determined by varying the angle of the detectors with respect to the normal.

24. A means for analyzing fluorescence from a fluorescent material, comprising (a) a film of fluorescent material adjacent to a waveguide, said waveguide having a corrugated surface which supports propagation modes for optical radiation at the wavelength of fluorescence and wavelength of absorption of said material, wherein the waveguide comprises a plurality of layers deposited on a grating, said plurality of layers including a layer of an electrically conductive, light reflective material forming said corrugated surface, a layer of a dielectric material disposed over the conductive, reflective material, and having a thickness between 20 nanometers and 500 nanometers, wherein the fluorescent emitting material is deposited on the layer of the dielectric material, and the dielectric material maintains the fluorescent emitting material spaced from the conductive, reflective material a distance of between 20 and 500 nanometers, (b) a means for exciting said propagation modes within said waveguide, (c) a means for detecting said fluorescence attributed to said propagation modes of said waveguide at their discrete angles of emission with respect to the film's normal, wherein said propagation modes excite the fluorescence of said material at discrete angles with respect to the normal to said film of said material, and the fluorescence is detected at the discrete angles by said detecting means, said fluorescence detected at said discrete angles being enhanced due to the concentration of said fluorescence at said discrete angles.

25. A means for analyzing according to claim 24 wherein said grating is an interference pattern formed by a layer of developed photoresist, mounted on a substrate.

26. A means for analyzing according to claim 24 wherein said grating is plastic and formed by a stamping process.

27. A means for analyzing according to claim 25 wherein said interference pattern is created using a recombined beam of a laser.

28. A means for analyzing according to claim 24 wherein said grating has uniform thickness across parallel planes normal to the surface and normal to the corrugation profile.

29. A means for analyzing according to claim 24 wherein grating surface of said grating consists of a superimposition of a number of parallel grated surfaces oriented at different angles with respect to a normal to the surface.

30. A means for analyzing according to claim 29 wherein the parallel grated surfaces superimposed to form said grating have differing periods of corrugation.

31. A means for analyzing according to claim 24 wherein the difference between maximum and minimum points on the surface of said grating along the surface normal is on the order of 50 nm.

32. A means for analyzing according to claim 24 wherein said layer of conductive material said layer of dielectric material, and said film of said fluorescent material are deposited by vacuum deposition techniques.

33. A means for analyzing according to claim 25 wherein said photoresist is deposited on said substrate by a spin method.

34. A means for analyzing according to claim 24 wherein said conductive material is reflective at the wavelengths at which fluorescence is excited and emitted.

35. A means for analyzing according to claim 24 wherein the thickness of each said film measured along a line normal to its surface is constant.

36. A means for analyzing according to claim 24 wherein said layer of conductive mateial is disposed on said grating.

37. A means for analyzing according to claim 36 wherein said layer of dielectric material has a predetermined thickness to separate the film of fluorescent emitting material from the layer of conductive material by a selected distance to maximize the enhancement at a particular wavelength of the fluorescence detected at discrete angels.

38. A means for analyzing according to claim 35 wherein the periodicity of corrugation profile of the grating is one the order of 0.1–1.0 micrometer.

39. A means for analyzing according to claim 36 wherein said layer of dielectric material is a transparent dielectric material and said fluorescent material contains an organic material.

40. A means for analyzing according to claim 39 wherein said dielectric material is LiF.

41. A means for analyzing according to claim 39 wherein said organic material is an organic fluorescent dye.

42. A means for analyzing according to claim 36 wherein said grating consists of a photoresist with a developed interference pattern with a period of 0.636 micrometer deposited on a glass substrate; said layer of dielectric material is LiF, of 20–500 nm thickness; said fluorescent material contains Rhodamine B, and said film of said fluorescent material is on the order of 0.3 nm.

* * * * *

UNITED STATES PATENT AND TRADEMARK OFFICE
CERTIFICATE OF CORRECTION

PATENT NO. : 5,006,716

DATED : April 9, 1991

INVENTOR(S) : Dennis G. Hall

It is certified that error appears in the above-identified patent and that said Letters Patent is hereby corrected as shown below:

In the Abstract, line 8: "fluorescence" should read as --fluorescent--

Column 4, lines 9-10: "fluorescent" should read as --fluorescence--

Column 9, line 63, Claim 16: "515.5" should read as --514.5--

Column 12, line 7, Claim 36: "mateial" should read as --material--

Column 12, line 18, Claim 38: "one" should read as --on--

Signed and Sealed this

Twentieth Day of October, 1992

*Attest:*

DOUGLAS B. COMER

*Attesting Officer*     *Acting Commissioner of Patents and Trademarks*